(12) United States Patent
Denton et al.

(10) Patent No.: US 8,210,166 B2
(45) Date of Patent: Jul. 3, 2012

(54) VIAL MULTI-ACCESS ADAPTER

(75) Inventors: Marshall T. Denton, Salt Lake City, UT (US); Timothy R. Wolfe, Salt Lake City, UT (US); Mark A. Christensen, Salt Lake City, UT (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 1637 days.

(21) Appl. No.: 10/737,656

(22) Filed: Dec. 16, 2003

(65) Prior Publication Data
US 2005/0131357 A1    Jun. 16, 2005

(51) Int. Cl.
*A61M 11/00* (2006.01)
(52) U.S. Cl. .................................. 128/200.14
(58) Field of Classification Search .......... 604/246, 604/275, 257, 27, 32, 411, 187, 30, 48, 248, 604/273; 137/625.41, 625.47, 859; 128/207.15, 128/207.18, 200.14, 200.15, 200.18
See application file for complete search history.

(56) References Cited

U.S. PATENT DOCUMENTS

| | | | |
|---|---|---|---|
| 3,818,911 A * | 6/1974 | Fournier | 604/1 |
| 3,874,381 A * | 4/1975 | Baum | 128/200.14 |
| 4,253,501 A | 3/1981 | Ogle | |
| 4,300,545 A * | 11/1981 | Goodnow et al. | 128/200.14 |
| 4,660,555 A * | 4/1987 | Payton | 128/207.18 |
| 4,765,588 A | 8/1988 | Atkinson | |
| 4,978,336 A * | 12/1990 | Capozzi et al. | 604/82 |
| 5,031,613 A | 7/1991 | Smith et al. | |
| 5,104,387 A | 4/1992 | Pokorney et al. | |
| D333,000 S | 2/1993 | Good et al. | |
| 5,233,979 A | 8/1993 | Strickland | |
| 5,246,012 A | 9/1993 | Strickland | |
| D340,185 S | 10/1993 | Martone | |
| D344,231 S | 2/1994 | Gagnon | |
| 5,284,132 A | 2/1994 | Geier | |
| 5,291,882 A | 3/1994 | Makhoul et al. | |
| 5,334,163 A | 8/1994 | Sinnett | |
| 5,429,600 A * | 7/1995 | Heinke | 604/516 |
| 5,433,191 A * | 7/1995 | Haber et al. | 128/200.14 |
| 5,490,630 A | 2/1996 | Hecker | |
| 5,511,538 A | 4/1996 | Haber et al. | |
| 5,601,077 A | 2/1997 | Imbert | |
| 5,803,078 A | 9/1998 | Brauner | |
| 5,964,223 A | 10/1999 | Baran | |
| 5,971,357 A | 10/1999 | Denton et al. | |
| 6,000,580 A * | 12/1999 | Nilson | 222/108 |
| 6,009,868 A | 1/2000 | Nilson | |
| D427,308 S | 6/2000 | Zinger | |

(Continued)

OTHER PUBLICATIONS

Official Gazette, p. 2224, Apr. 15, 1997.

*Primary Examiner* — Kevin C Sirmons
*Assistant Examiner* — Andrew Gilbert
(74) *Attorney, Agent, or Firm* — TraskBritt (57) ABSTRACT

A multi-access adapter operable to dispense doses of a medicament in succession from a bulk container, such as a vial. A preferred adapter may be used alone, or in combination with various discharge devices. A first preferred combination includes the adapter paired with a needle for injection of the medicament into one or more patients. A second preferred combination includes an atomizing nozzle affixed to the adapter and arranged for discharge of the medicament therethrough. Sometimes the atomizing nozzle carries a nostril guide structure that can be absorbent and may operate as a splash guard.

6 Claims, 5 Drawing Sheets

U.S. PATENT DOCUMENTS

| | | |
|---|---|---|
| 6,079,413 A | 6/2000 | Baran |
| 6,112,743 A | 9/2000 | Denton |
| 6,224,346 B1 | 5/2001 | Denenburg |
| 6,228,070 B1 * | 5/2001 | Mezzoli ................ 604/257 |
| 6,238,372 B1 * | 5/2001 | Zinger et al. ............ 604/246 |
| 6,379,340 B1 | 4/2002 | Zinger et al. |
| 6,386,197 B1 * | 5/2002 | Miller ................ 128/206.11 |
| 6,526,976 B1 | 3/2003 | Baran |
| 6,543,703 B2 | 4/2003 | Blake |
| 6,575,944 B1 | 6/2003 | McNary |

\* cited by examiner

VIAL MULTI-ACCESS ADAPTER

BACKGROUND OF THE INVENTION

1. Field of the Invention

The invention relates to devices for extracting a dose of a fluid from a sealed fluid container. The invention finds particular application in the medical field, providing multiple-dose extraction from vials or ampules, by incorporating a syringe as a cyclical pump.

2. State of the Art

Several devices have been developed to facilitate transfer of a dose of a liquid from a bulk container. In the medical field, certain of such devices may be used to transfer a dose of a medicament from a vial, or a bulk container of medicament, to a syringe for injection or administration of the dose to a patient. In some situations, it is desirable to transfer more than one dose of medicament from the container in rapid succession. Ogle, in U.S. Pat. No. 4,253,501, discloses a transfer system having a manually controlled valve and permitting successive withdrawals of a medicament from a bulk container using a syringe for administration of the medicament to a patient. Ogle's manual valve requires adjustment to a first position to permit withdrawal of a dose, or filling the syringe. Then, the valve must be adjusted, manually, to a second position to permit fluid flow from the loaded syringe for administration of the fluid to a patient. While operable, Ogle's device suffers from the requirement for a user to make manual valve adjustments to load and discharge a syringe.

Synnett discloses an apparatus in U.S. Pat. No. 5,334,163 that is adapted to withdraw doses of a pressurized gas from a bulk container for injection of that gas into body tissue with a syringe. Synnett provides a three way valve that requires a manual adjustment to select a desired flow path between the container, the syringe, and an ejection conduit.

Zinger, in U.S. Pat. No. Des. 427,308, discloses an ornamental design for a vial adapter operable to pierce a seal carried by a container of a medicament. Zinger's vial adapter includes a spike which could be operable to pierce a seal membrane, and also has gripping structure that appears to be disposed to hold the container. The adapter disclosed in this patent is of the type that may be connected directly to a syringe, through a LUER-LOK™ type of connection, for withdrawal of a dose of fluid to fill the syringe with the desired dose of medicant fluid. Then, the adapter is removed from the syringe, and a discharge element may be affixed to the syringe, prior to administering the dose to a patient.

In U.S. Pat. Nos. 6,238,372 and 6,379,340, Zinger discloses a fluid control device adapted for attachment to a syringe and operable to withdraw a dose of medicament from a container, such as a vial having a punch-through sealing membrane. The disclosures of these patents are hereby incorporated herein, as if set forth in their entirety, for their teachings of vials and adapters. Zinger's disclosed embodiments include a valve member having a core that is manually positioned, by rotating it, to select a fluid flow path between the container, syringe, and an ejection conduit.

Figure 1:
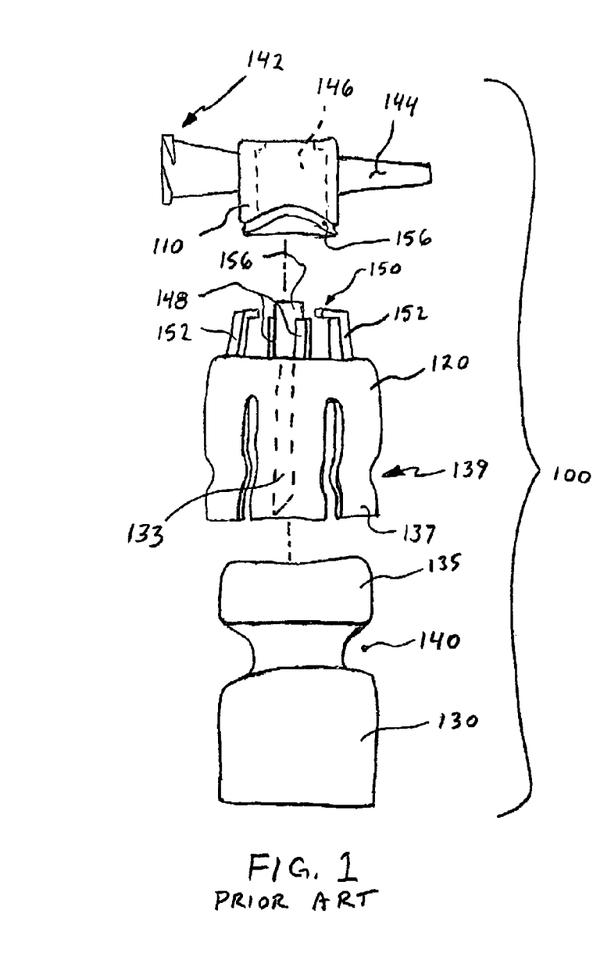
FIG. 1 is an exploded assembly view in elevation of a prior art vial adapter assembly.

A commercially available embodiment of Zinger's device is generally indicated at 100 in FIG. 1. A flow path through conduit 110 is selected either by attaching the conduit 110 to, or removing it from, socket 120. Socket 120 can be placed into engagement with a vial 130 to pierce spike 133 through a membrane seal (not illustrated) in cap 135. A plurality of legs 137 each carry gripping structure, generally indicated at 139, arranged to hold vial 130 at a neck area 140 to resist removal of spike 133 from engagement with the vial 130. A first end of conduit 110 carries connection structure, generally indicated at 142, adapted for attachment to a syringe. A second end of conduit 110 carries a surface 144 adapted to form a slip fit with a needle, or other discharge device.

The flow path through conduit 110 is selected by a rotated position of core 146. As conduit 110 is placed into engagement with socket 120, wrench structure 148 engages into receiving socket structure (not illustrated) in core 146, and causes core 146 to rotate. Male thread structure, generally indicated at 150, carried by cantilevered arms 152 engages female thread 156 to alternately engage, and release, conduit 110 with respect to socket 120. At a first attached position, fluid can be extracted through nipple 156 to fill a syringe attached to structure 142. Successive 180 degree rotations of socket 120 with respect to conduit 110 can either release or re-engage the two components. Such rotations effect corresponding rotations of core 146, and thereby also selects a flow path through the conduit 110. At a second attached position, with core 146 rotated by 180 degrees from the first position, the core 146 blocks the flow path from the syringe. A syringe attached to structure 142 can only be discharged if conduit 110 is removed from the socket 120.

One embodiment of a vial adapter disclosed in the '372 patent, and illustrated in its FIGS. 3 and 4, can be oriented for discharge of a syringe while the syringe is attached to a vial. However, a manual adjustment must be effected to change a valve orientation. The device must be manually rotated to change a valve configuration subsequent to filling the syringe with the desired dose of fluid.

Situations occur that require dispensing successive doses of the same medicament to one or more patients. In a military application, repetitive injections may be required by needle during battlefield conditions, or to administer mass inoculations. In nasal therapy, an atomizer is typically employed to dispense multiple applications of a medicant, e.g. to one nostril, then to the other nostril for the same patient.

It would be an improvement in the art of dispensing medicaments to provide an adapter to interface with a bulk container of medicanent and operable to permit dispensing successive doses of that medicament simply by operation of a syringe. It would be a further improvement to provide an adapter operable either as a nasal treatment device, or as an injection dispensing apparatus. A further improvement would include a guide structure at a discharge end of the nasal treatment device to space the discharge orifice from a nostril wall. A still further improvement would provide an absorbent guide structured as a splash shield.

BRIEF SUMMARY OF THE INVENTION

A multi-access adapter operable to dispense doses of a fluid in succession from a bulk container. The adapter may be used alone, or in combination with various discharge orifices. A first preferred combination includes the adapter paired with a needle for injection of the fluid into one or more patients. A second preferred combination includes an atomizing nozzle affixed to the adapter and arranged for discharge of the medicament therethrough. Sometimes the atomizing nozzle carries a nostril guide structure that can be absorbent and may operate as a splash guard. Preferred atomizers include a nozzle carried at an end of an extension conduit that can be configured, by bending, to orient a direction of discharge from the atomizer nozzle.

A currently preferred multi-access adapter is adapted to withdraw consecutive doses of fluid from a vial. Such an adapter includes a spike configured for insertion into a vial access port and operable to withdraw fluid from inside the vial. Holding structure may be configured as a socket carrying the spike and adapted to grip the vial to resist withdrawal of the spike from the access port. The adapter also includes a first automatic check valve attachable to the socket and disposed in a first flow path between the spike and a staging zone. The adapter typically is used in combination with a syringe affixed in fluid communication with the staging zone.

Conduit structure is provided to define a second flow path from the staging zone to a discharge orifice. In general, a second automatic check valve is included in the second flow path. Certain embodiments include a needle as a portion of the second flow path. Alternative embodiments include an atomizing nozzle in the second flow path. Sometimes, the second flow path includes an extension conduit having a user-configurable shape. A shape in such a conduit may be defined, at least in part, by a deformable element associated with, and operable to maintain a shape in, the extension conduit. A currently preferred extension conduit includes a deformable wire disposed in one of a plurality of lumens through the extension conduit. The wire maintains a deformed shape in the extension conduit whereby to define a direction of fluid discharge from a nozzle discharge orifice.

When embodied as an atomizer for nasal treatment, a nostril guide may be arranged to space a conduit portion of the atomizing nozzle apart from structure forming an entrance to a nostril. Portions of certain nostril guides are sometimes capable of absorbing fluid. Nostril guides may also be configured for their operation as a splash guard. A polymer material, such as a porous, hydrophilic, Styrene-Butylene-Rubber copolymer can be arranged to form an exemplary nostril guide.

Desirable nostril guides provide a distal portion having a shape with an increasing cross-section size corresponding to increased insertion depth, whereby to adapt to a variety of nostril sizes, and to form a brace against nostril structure operable to maintain an orientation of the nozzle while operating the syringe. Workable nostril guides can be arranged to form a substantially bullet shape. One preferred guide is arranged as a conical plug with a diameter ranging between about 0.2 inches and about 0.8 inches.

The invention can also be embodied as an adapter of the type including a base carrying a spike that provides access through which to withdraw a fluid from a container. The base of the adapter further carries holding structure depending from the base and structured as a socket operable to resist separation between the spike and a container into which the spike is inserted. Such an adapter generally has a base formed from a first material and a socket formed from a second material. The second material desirably is more resilient than the first material to permit an increase in a diameter of a circumferentially oriented wall of the socket to form a self-biased holding interface between the socket wall and held portions of containers. The tubular socket can expand to hold different sized containers.

Typically, an adapter's base is formed from a substantially rigid medical grade plastic configured and arranged to provide a foundation. A workable socket can be formed from a length of resilient tubing affixed to the foundation to expose an open end of the tubing. A container can then be jammed into the open end of the tubing to expand a diameter of the socket and to form a holding interface between the tube wall and a held portion of the container. In one currently preferred embodiment permitting multi-dose extraction from the container, the base further includes a valve operable as a double check valve arranged to permit fluid flow in a first flow path from an orifice of the spike toward a staging area and to resist fluid flow in a reverse direction.

BRIEF DESCRIPTION OF THE SEVERAL VIEWS OF THE DRAWINGS

In the drawings, which illustrate what are currently considered to be the best modes for carrying out the invention.

DETAILED DESCRIPTION OF THE ILLUSTRATED EMBODIMENTS

Figure 2:
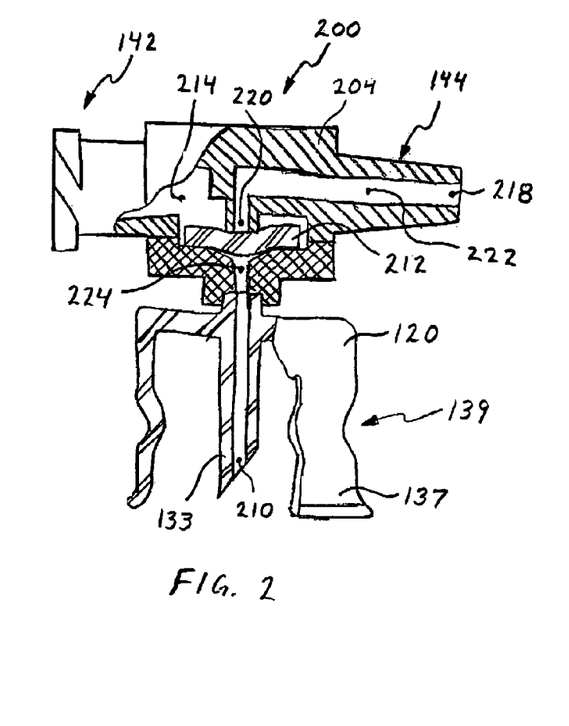
FIG. 2 is a view in elevation, partially in section, of a currently preferred embodiment of a multi-access adapter.

A currently preferred embodiment of the invention, indicated generally at 200, is illustrated in FIG. 2. The vial multi-access adapter 200 includes a socket 120 carrying a spike 133 and a plurality of cantilevered legs 137. Legs 137 include grasping structure 139 adapted to hold a vial to help maintain its reception on a spike 133. While the plurality of legs 137 are illustrated in the FIGs. as forming a substantially complete circle, even a single opposed pair of legs 137 can be operable as gripping structure. A valve 204, operable as a double check valve, is attached in fluid communication with the spike 133. A first end of valve 204 carries connection structure, generally indicated at 142, adapted for attachment to a syringe. A second end of valve 204 carries a surface 144 that typically is adapted to form a conventional slip fit with the luer of a needle, or other discharge device.

When adapter 200 is mated to a vial, fluid from the vial may be suctioned by an attached syringe through an entrance orifice 210 of spike 133, past a resilient seal element 212 disposed in a first flow path, to a staging zone or area 214. A staging zone or area 214 may generally be regarded as being defined by a volume in which to hold a dose of treatment fluid extracted from a vial in preparation to ejection of the dose from the device. Pressure at the staging area typically alternates between a relative low value and a relatively high value under the influence of an attached syringe employed as a pump. A dose of fluid extracted from the vial can then be ejected from the staging area 214, past the resilient seal element 212 disposed in a second flow path, and toward a discharge orifice 218.

Valve 204 operates automatically as a double check valve under conditions of its typical use. Valve 204 may also be characterized as a check-bypass valve, in that fluid flow may be caused through one flow path in either direction by appropriate pressure conditions. For purpose of this disclosure, automatic operation means that actuation of the valve occurs under the influence of hydraulic pressure. The illustrated valve 204 operates without requiring manual manipulation of valve elements to permit fluid flow.

In an assembled valve 204, seal element 212 is self-biased into engagement of one surface over an entrance 220 to discharge conduit 222. An opposite side of seal 212 is simultaneously biased to cover an entrance port 224 to the valve 204. A suction applied by a syringe tends to further urge the seal 212 into sealing engagement over opening 220, and also urges fluid to flow through entrance 224, past a perimeter of seal 212, and toward the staging zone 214. A pressure applied by a syringe to fluid in the staging zone 214 can cause a deflection of seal 212 into enlarged entrance port 224 sufficient to cause an opening between discharge entrance 220 and seal 212, thereby permitting fluid flow toward the discharge orifice 218.

With reference to the structure illustrated in FIG. 2, it should be recognized that high pressure fluid applied to discharge conduit 222 may flow past seal member 212 toward a lower pressure at the staging zone 214. Therefore, the illustrated valve 204 may properly be regarded as a check-bypass valve. However, in conditions of typical use, the valve 204 operates as a double check valve. Valves having other configurations, including true double check valves that resist fluid flow in one direction, are operable in the invention. An operable automatic valve arrangement desirably permits cyclic operation of a syringe to dispense successive doses of fluid without requiring direct manual manipulation of valve structure. For purpose of this disclosure, the term "double check valve" is intended to include any valve arrangement operable as a double check valve, including a plurality of cooperating single check valves and the aforementioned check-bypass valve.

Figure 3:
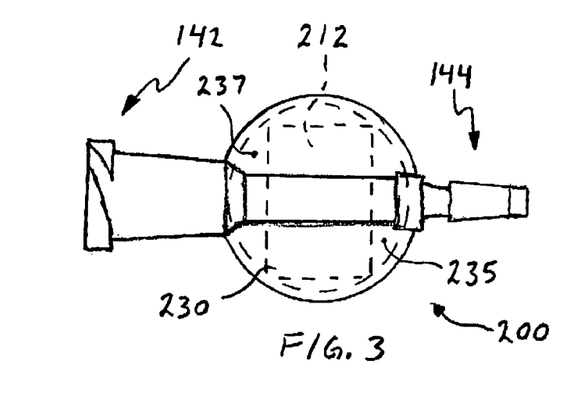
FIG. 3 is a top view of the embodiment illustrated in FIG. 2.
Figure 4:
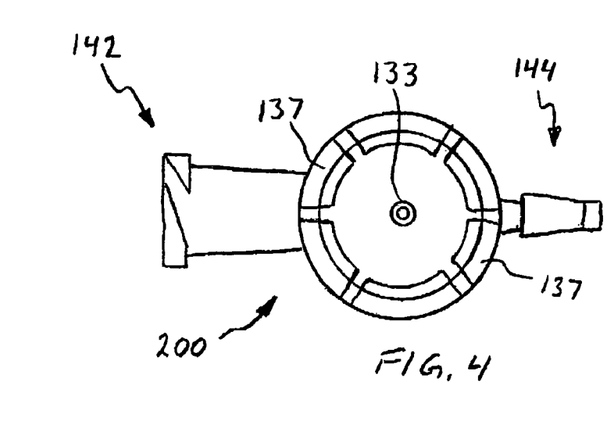
FIG. 4 is a bottom view of the embodiment illustrated in FIG. 2.

FIGS. 3 and 4 illustrate top and bottom views of a currently preferred adapter, respectively. Proximal attach structure 142 typically is arranged as a portion of a LUER-LOK™ type joint, although any other structure operable to connect to a syringe can be used. Distal attach structure 144 can be arranged to form a conventional slip fit with an extension structure, or may be configured to receive extension structure in substantially permanent attachment.

With reference to FIGS. 2 and 3, seal element 212 may be embodied as a wafer having a multi-sided cross-section shape for reception in an ovaloid chamber. Corners 230 of seal 212 assist in maintaining seal 212 somewhat centered in the chamber 235. Gaps 237 between seal 212 and chamber 235 permit fluid flow under suction from spike entrance 210 toward the staging area 214. An exemplary seal element 212 may be made from silicone rubber, or, from a similarly resilient material. Housing portions of valves 204 and sockets 120 of adapters 200 may be made from medical grade plastics. Adapters 200 typically include injection molded components. While the embodiment illustrated in FIG. 2 is assembled to form a unitary, substantially rigid structure, it is also within contemplation to provide an extension conduit or tube (which may be flexible) disposed between vial adapter socket 120 and a double check or check-bypass valve, such as a valve 200.

Figure 5:
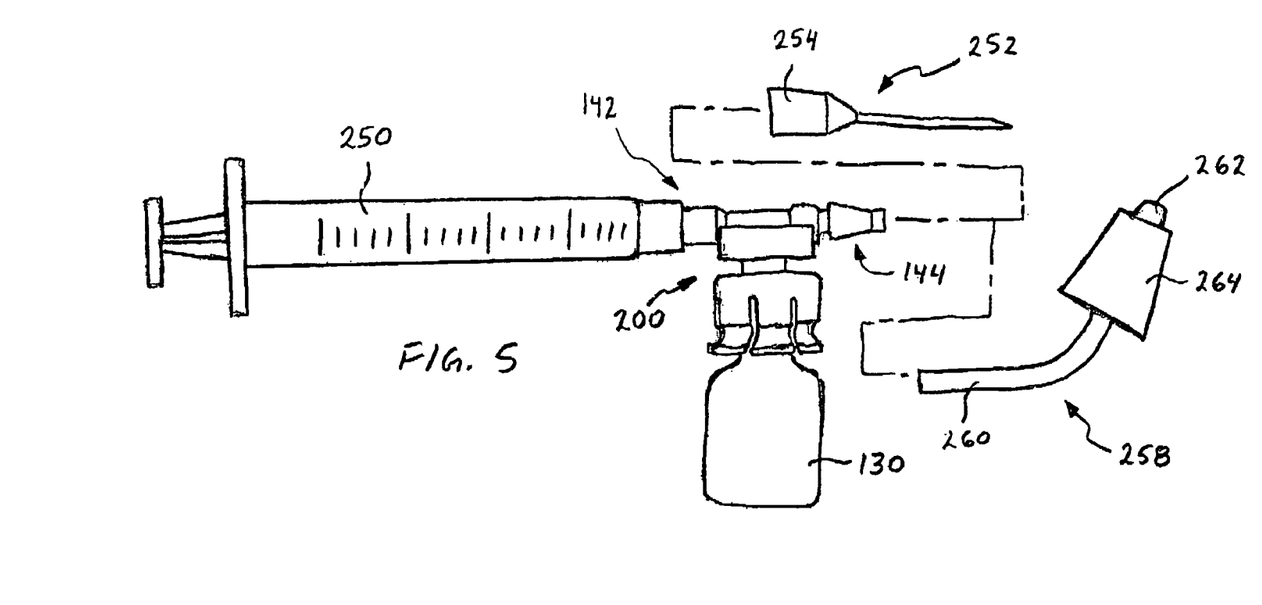
FIG. 5 is a view in elevation of combinations illustrating alternative aspects of the invention.

FIG. 5 illustrates alternative assemblies that can benefit from use of the invention 200. A syringe 250 is attached to a vial adapter 200 at proximal connection structure 142. Such an assembly may be used with extension conduit structure adapted to perform many desired tasks. As a first example, needle 252 may be affixed by way of a slip fit between a bore in hub 254 and distal attach structure 144 to permit injecting one or more patients with one or more doses extracted from a vial 130. As a second example, an atomizer 258 may be affixed to distal structure 144 to administer successive doses of fluid from vial 130 in a misted form. Other alternative extension conduits may be adapted to form a discharge stream like a squirt gun, rather than a mist.

Figure 6:
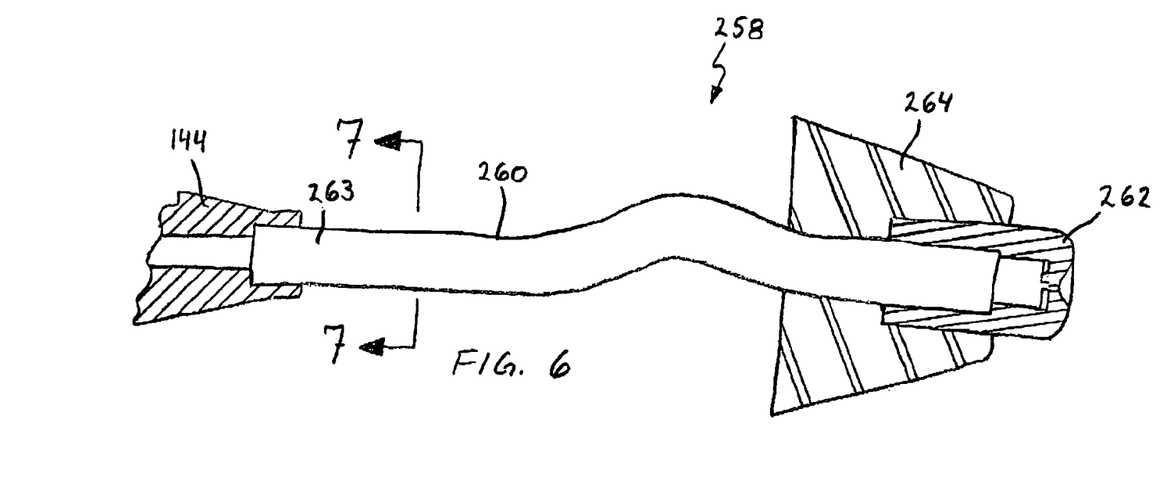
FIG. 6 is a view in elevation, partially in section, of a currently preferred discharge nozzle attached to a discharge portion of the invention.

With reference to FIGS. 5 and 6, a currently preferred atomizer includes a conduit extension 260 carrying an atomizing nozzle 262 at a distal end. A proximal end 263 can be attached to a distal end of attach structure 144 by adhesive bonding, or welding, as illustrated in FIG. 6. An alternative attachment structure (e.g. a luer slip-fit arranged similarly to hub 254 of illustrated needle 272), may also be employed removably to attach conduit to a valve 200. Nozzle 262 is configured to impart a rotational component of velocity in discharged fluid in accordance with known atomizing nozzles.

A nostril guide 264 may be included for embodiments used in nasal therapy. A guide and nozzle arrangement as illustrated in FIG. 6 can be used in nasal therapy for patients having nostrils sized between newly born to large adult. A nostril guide 264 may be installed onto conduit 260 with a press fit, or may be bonded. Guides 264 desirably are absorbent, or include an absorbent portion, to soak up dripping or excess fluid. A currently preferred nasal guide is made from a polymer material, such as a porous, hydrophilic, Styrene-Butylene-Rubber copolymer. Other materials are also workable, such as cotton, or other natural or man-made materials.

Figure 7:
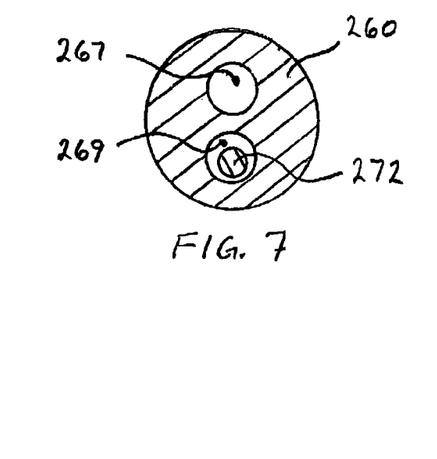
FIG. 7 is a view of a cross-section of the embodiment illustrated in FIG. 6, taken through the section designated 7-7.

Conduit 260 may be any convenient length, although many will have a length between about 1½ and about 6 inches. The length of extension conduit 260 may be based upon a particular application. For example, in tracheal therapy applications, conduit 260 may be about 6 inches to about 12 inches long, or more. In nasal therapy applications, a convenient length may be significantly shorter; perhaps only about ½ inch. Certain conduits 260 are deformable to permit orienting a direction of discharge from the nozzle 262. As illustrated in FIG. 7, one operable deformable conduit 260 includes a plurality of lumens 267 and 269, with a deformable element 272 being carried in lumen 269. Of course, conduit 260 may have any number of internal lumens, including just one lumen. Element 272 can be a metal wire, or any structure capable of holding a deformed shape, and holding a deformed shape in conduit 260. A deformable element may also be affixed to an exterior of conduit 260, or may even constitute the conduit 260.

Figure 8:
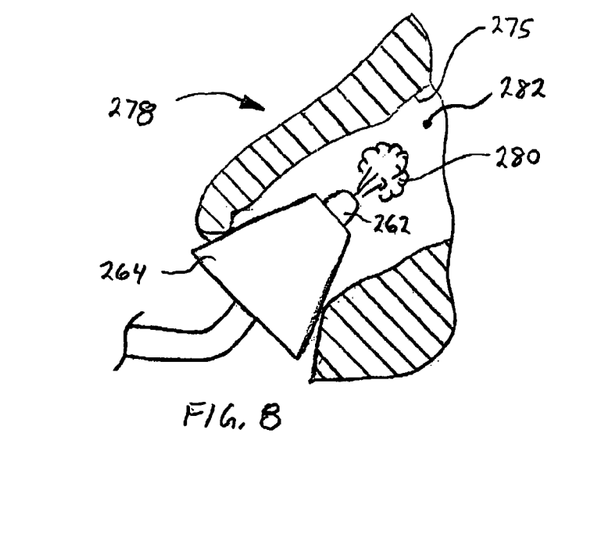
FIG. 8 is a portion of the embodiment of FIG. 6 in use to dispense a mist into a nostril that is illustrated in cross-section.

With reference now to FIG. 8, a nostril guide is illustrated in use to position a discharge from nozzle 262 spaced apart from wall 275 of a nostril, generally indicated at 278. Guide 264 desirably is employed to stabilize nozzle 262 during actuation of a syringe to spray a discharge mist 280 into nasal passage 282, and to avoid spraying mist 280 directly into the wall 275. Desirable guides 264 are configured at their distal portions to brace against nostril structure, in a structural interference, to hold an atomizing nozzle steady while a syringe is operated.

A distal portion of a guide 264 desirably is structured to provide a variable size cross-section that increases in correspondence with an insertion depth into the nostril 278 to space a conduit portion apart from an entrance to the nostril. One desirable shape for guide distal structure is similar to that of a bullet. Workable guides 264 can even have distal portions that are substantially round, like a ball. A guide 264 can be arranged as a conical stopper or plug with a diameter ranging between about 0.2 inches on a distal end and about 0.8 inches at a proximal portion. Certain preferred guide shapes also function as a splash shield to resist splash back of an administered dose of fluid.

Figure 9:
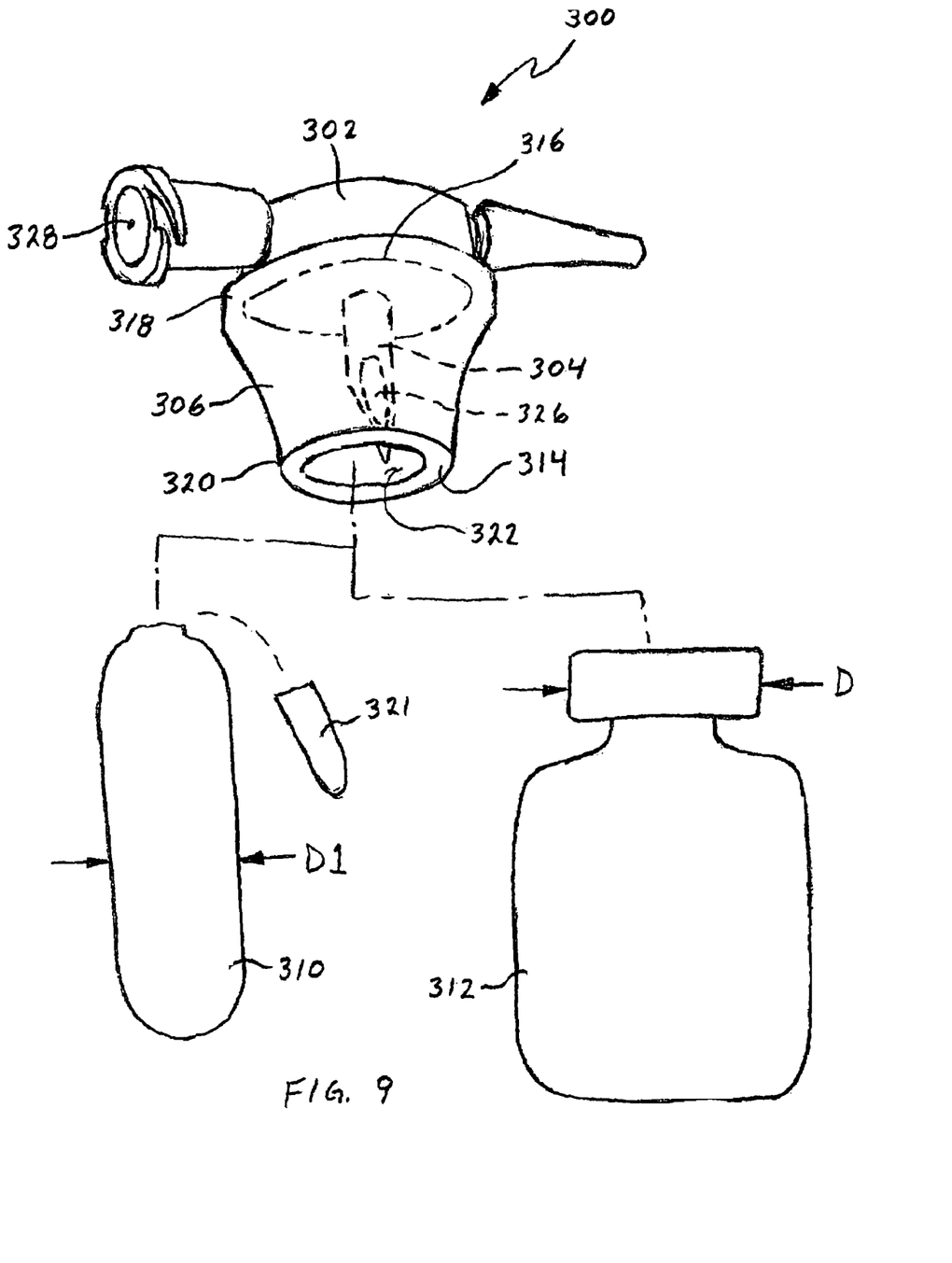
FIG. 9 is a bottom view in perspective an embodiment of a vial multi-access adapter with alternative holding structure that is adapted for gripping either of an ampule or a vial, the latter containers being illustrated in side views in elevation.

As illustrated in FIG. 9 and generally indicated at 300, the invention can also be embodied as an adapter of the type including a base 302 carrying a spike 304 that provides access through which to withdraw a fluid from a container. The base 302 further carries holding structure 306 depending from the base 302. Holding structure 306 is structured as a socket operable to resist separation between the spike 304 and a container, such as ampule 310 or vial 312, into which the spike 304 is inserted. The base 302 typically is formed from a first material and the socket 306 generally is formed from a second material. The second material desirably is more resilient than the first material to permit an increase in a diameter of circumferentially oriented wall 314 of the socket 306 to form a self-biased holding interface between the socket wall 314 and held portions of containers. Therefore, tubular socket 306 can expand to form a self-biased interface with different size held portions D1 and D2 of different containers.

Typically, base 302 is formed from a medical grade plastic configured and arranged to provide a foundation 316. Typically, a base 302 will be injection molded. A workable socket 306 can be formed from a length of tubing affixed at end 318 to the foundation 316 to expose an open end 320 of the tubing. Illustrated socket 306 is adhesively bonded to foundation 316. A molded-in capture lip arrangement between a base 302 and a socket 306 is also within contemplation. A socket 306 can be formed as a segment cut from a length of a "stretchy" material, such as silicone rubber or urethane tubing. It is also within contemplation for a socket to be molded or cast. A container, such as ampule 310 (after neck closure 321 is snapped-off) or vial 312, can be jammed into the open end 320 of the tubing to expand a diameter of the socket 306 and to form a holding interface between an inner surface 322 of the tube wall 314 and a held portion of the container.

In one currently preferred embodiment permitting multi-dose extraction from the container, the base 302 further includes a valve, such as valve 200 (see FIG. 2), operable as a double check valve. The valve 200 desirably is arranged to permit fluid flow in a first flow path from an orifice 326 of the spike 304 toward a staging area 328 and to resist fluid flow in a reverse direction.

It should be noted that the adapters illustrated in FIGS. 2-5 and 9 are operable as illustrated, and particularly for small treatment doses. However, it has been found that performance of the illustrated devices can further be improved by the addition of an automatic bypass valve (not illustrated) arranged as a check valve to permit entrance of replacement air into a vial to facilitate extraction of treatment fluids. Such a bypass valve is particularly beneficial when the treatment dose to be extracted constitutes a significant percentage of the volume of the vial (e.g. more than about 3-5 ml). In the absence of an air bypass valve, the syringe tends to entrain air along with the fluid dose. While the entrained air may preferentially be ejected from the device prior to dispensing the dose of fluid, such an extra step is less convenient than is generally desired.

Figure 10:
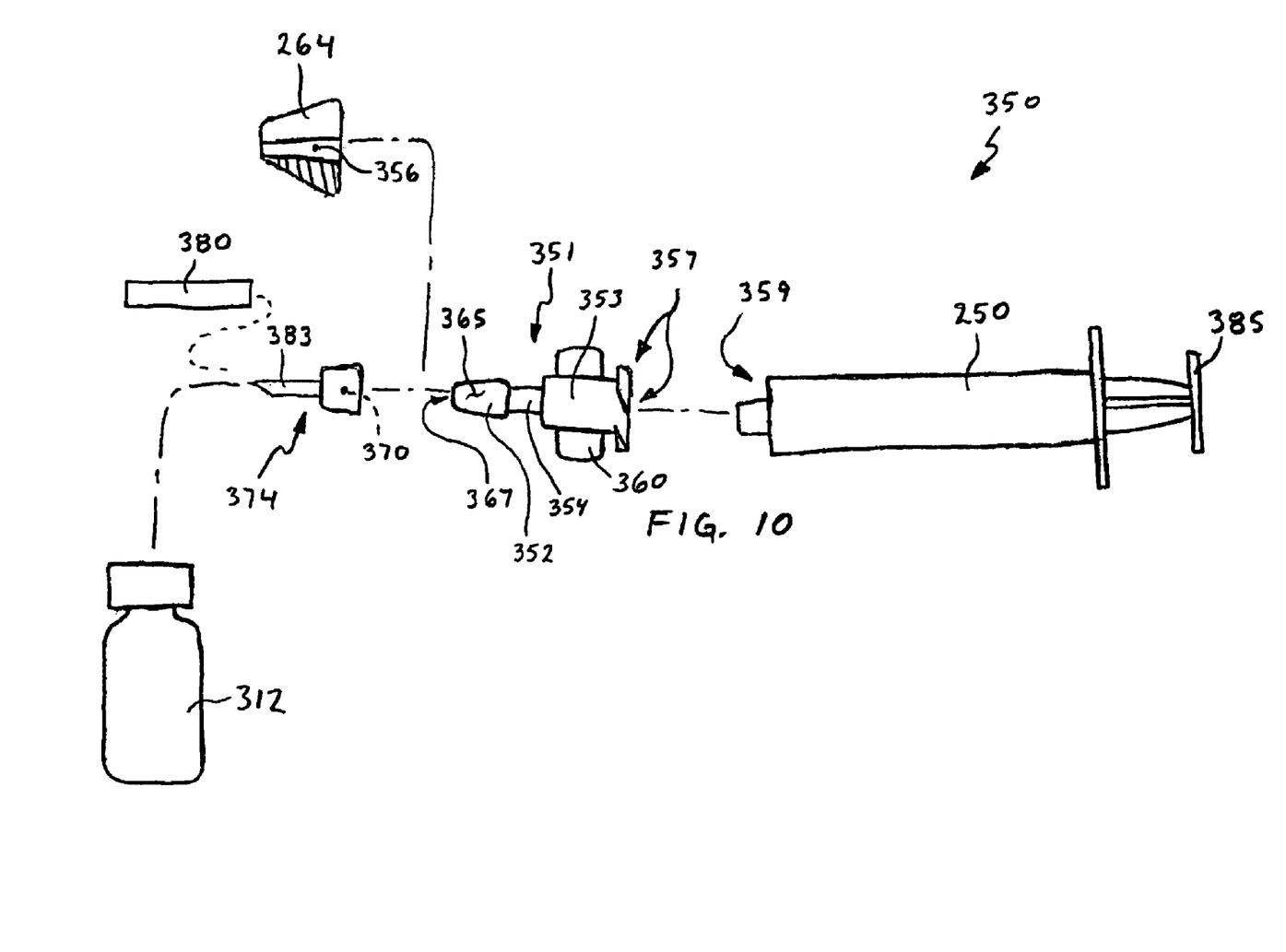
FIG. 10 is an exploded assembly view, partially in section, of a preferred multi-access arrangement.

FIG. 10 illustrates an alternative and currently preferred embodiment of a multi-access adapter arrangement, generally indicated at 350. The arrangement 350 includes some sort of atomizer, such as the atomizer generally indicated at 351, in fluid-flow association with a pump, such as syringe 250. Sometimes, a nostril guide 264 is included and may be installed by placing tunnel 356 over the distal end of the atomizer 351.

Illustrated atomizer 351 includes an atomizing nozzle 352 spaced apart from a hub 353 by an extension conduit 354. Conduit 354 can have a range in length and conformation corresponding to the intended use of the device 350, similarly to the extension conduit 260 (FIGS. 5 & 6). A fluid-flow association between a syringe 250 and an atomizer 351 typically is accomplished by connecting cooperating female and male structure, generally indicated at 357 and 359 respectively, forming a slip-fit connection, such as the illustrated luer-locking joint. Wings 360 facilitate twisting threaded luer-locking structure into and out-of engagement.

The illustrated atomizer 351 provides a seal surface 365 disposed near a discharge orifice, generally indicated at 367. Seal surface 365 is adapted to form a slip-fit connection with cooperating structure, such as socket 370, carried at one end of the extraction device generally indicated at 374. Illustrated surface 365 has a taper to fit a common luer taper typically provided in a socket 370. Of course, it is within contemplation simply to jam a suitably sized nozzle into reception inside receiving structure of an extraction device, such as socket 370 of device 374. A cooperating taper is not even required between the extraction device and an atomizing nozzle or other fluid conducting structure associated with a syringe. A vacuum formed as the syringe is loaded helps to maintain a fluid-tight connection between the components.

Extraction devices 374 are operable to conduct fluid from the inside of a storage container, such as vial 312 or ampule 310 (see FIG. 9), toward the syringe 250. Workable extraction devices include metal and plastic needles and connectors, with needles of the "stickless" type being most preferred for increased safety of health practitioners. One such stickless needle/connector is commercially available from Emergency Medical Products, Inc. under the catalog No. NF9285 and the trade name "Medic (R) Plastic Anti-stick Needle". An alternative workable extraction adapter 374 can be made from a straw or a length of tubing.

Atomizers, such as illustrated atomizer 351, operate by imparting a spin to a fluid stream prior to ejecting the stream through a discharge orifice to form a mist. Atomizers typically have small diameter discharge orifices to help create a fine mist of discharged fluids by providing a pressure drop across the orifice. Surprisingly, it has been determined that it is neither too difficult nor too slow to load a fluid dose into an atomizer by suction of the dose (backwards) through the atomizer's discharge orifice.

During a portion of the operation of certain embodiments of the instant invention, a fluid dose may be regarded as following a flow path from a storage vial 312 or ampule 310 toward a suction device, such as a syringe 250. A portion of the flow path may be regarded as being defined by structure provided by an element such as tunnel 356 in guide 264, discharge orifice 367 in atomizer 351, or conduit 224 of automatic check valve 200 (FIG. 2).

Typically, the multi-access arrangement 350 will be used as follows: A syringe 250 is attached to an atomizer 351. An extraction needle 374 is placed into engagement on seal surface 365, and a protective sleeve 380 (if so equipped) is removed to expose the needle 383. Needle 383 is placed through a rubber-like seal at the top of vial 312, and plunger 385 of syringe 250 is retracted to suction a dose of fluid from the vial 312. Seal surface 365 is removed from socket 370, and the dose of treatment fluid may then be dispensed to a treatment site of a patient by aiming the discharge mist and depressing the plunger 385. In certain cases, a nostril guide 264 may be placed over the dispensing end of the atomizer 351 prior to extracting a dose of fluid from vial 312. It should be noted that typically at least a sufficient portion of surface 365 will protrude distally from, or be accessible in, the guide 264 to permit joining to an extraction device 374. In general, the device 374 can be left in engagement in the vial 312. A second or subsequent dose conveniently may be extracted from the storage container by reconnecting seal surface 365 to the extraction device 374 and repeating the dose extraction procedure.

What is claimed is:

1. In an atomizer of the type used in nasal therapy and including a syringe adapted to urge a therapeutic dose of fluid from a proximal end toward a distal end of an extension conduit for discharge of that fluid as a mist from an atomizing nozzle that is structured to impart spin to a fluid just prior to expelling that fluid through an orifice, the improvement comprising:
   a nostril guide structure configured as an enlarged stopper affixed at said distal end of said extension conduit and arranged to space said nozzle apart from structure of a nostril entrance, said nostril guide structure comprising an absorbent portion; wherein:
   said atomizer is arranged in combination with;
   a vial multi-access adapter operable to extract said dose from a bulk container of therapeutic fluid through an automatic check valve for subsequent discharge of said dose from said atomizer.

2. The improvement of claim 1, wherein:
   a distal portion of said nostril guide is configured to brace in structural interference on opposite sides of a nostril opening, effective to steady said nozzle during operation of said syringe.

3. The improvement of claim 1, wherein:
   said absorbent portion of said nostril guide comprises a polymer material configured to brace in structural interference on opposite sides of a nostril opening.

4. The improvement of claim 1, wherein:
   said nostril guide comprises a porous, hydrophilic, Styrene-Butylene-Rubber copolymer.

5. The improvement of claim 1, wherein:
   said nostril guide comprises a stopper configuration that is operable as a splash-shield.

6. An atomizer of the type used in nasal therapy and including a syringe adapted to urge a therapeutic dose of fluid from a proximal end toward a distal end of an extension conduit for discharge of that fluid as a mist from an atomizing nozzle, in operable combination with a vial multi-access adapter, wherein:
   said vial multi-access adapter comprises a discharge orifice in fluid communication with said proximal end of said extension conduit, said multi-access adapter comprising:
   a spike configured for insertion into an access port of a bulk medicament container and operable to withdraw fluid from inside said container;
   a holding structure carrying said spike and adapted to couple with said container whereby to resist withdrawal of said spike from said access port;
   an automatic valve comprising a first check valve portion and a second check valve portion, said first check valve portion being disposed in fluid communication with an inlet opening of said spike and arranged to form a portion of a first fluid flow path between said inlet opening and a staging zone, said first check valve portion being operable to resist fluid flow from said staging zone to said inlet opening; and
   structure defining a second fluid flow path from said staging zone to said discharge orifice, wherein:
   said second check valve portion is disposed in said second flow path, and is operable to resist fluid flow from said discharge orifice to said staging zone; and further in combination with:
   said syringe disposed to cause pressure fluctuation in a fluid at said staging zone, said syringe being configured to aspire fluid from said vial for entrance of a dose of said fluid in a forward direction through an opening into a body of said syringe, and to expel said dose in a reverse direction through said opening and toward said discharge orifice.

* * * * *